United States Patent

Ohashi et al.

Patent Number: 5,466,442
Date of Patent: Nov. 14, 1995

[54] CHOLESTERYL SILICONE DERIVATIVE AND COSMETIC COMPOSITION COMPRISING THE SAME

[75] Inventors: Yukihiro Ohashi; Akira Kawamata, both of Utsunomiya, Japan

[73] Assignee: Kao Corporation, Tokyo, Japan

[21] Appl. No.: 173,471

[22] Filed: Dec. 27, 1993

Related U.S. Application Data

[63] Continuation of Ser. No. 913,719, Jul. 16, 1992, abandoned.

[30] Foreign Application Priority Data

Jul. 19, 1991 [JP] Japan ................................. 3-179695

[51] Int. Cl.[6] ................................................ A61K 7/06
[52] U.S. Cl. ..................... 424/70.12; 424/401; 556/443
[58] Field of Search ................................. 556/347, 443; 424/70.12

[56] References Cited

U.S. PATENT DOCUMENTS

| | | | |
|---|---|---|---|
| 3,515,734 | 6/1970 | Craig | 556/437 |
| 4,358,391 | 11/1982 | Finkelmann et al. | 252/299.01 |
| 4,906,458 | 3/1990 | Shigeta et al. | 514/772 |
| 5,106,530 | 4/1992 | Haas et al. | 555/437 |
| 5,144,054 | 9/1992 | Shioya et al. | 556/445 |

FOREIGN PATENT DOCUMENTS

| | | |
|---|---|---|
| 0362860 | 11/1990 | European Pat. Off. . |
| 0446938 | 9/1991 | European Pat. Off. . |

OTHER PUBLICATIONS

Derwent Abstract of JP 3005488 91/01/11.
Derwent Abstract of JP 890254861 89/09/29.
Derwent Abstract of JP 3005488 91/01/11.
CA 115 (24): 263054w Jpn Kokai Tokkyo Koho May 20, 1991.
CA 112(4): 21551b Stegemeyer.
CA116 (4): 22/05D Shashi et al Mar. 15, 1991.
CA 115(10): 98969P Ohashi.
CA 116:224894w Iida, S. et al.
File Supplier PAJ/JP0 & JP-A-4066513, "New—Siloxane—Derivative, Oil For—Cosmetic-Containing the Same and—Cosmetic—".
File Supplier PAJ/JP0 & JP-1-3005488, "Ester—Modified—Silicone—Derivative and—Cosmetics—Containing the Same Compound".
File Supplier PAJ/JP0 & JP-A-2101083, "Alcochol–Modified—Silicone—Ester Derivative and—Cosmetic—Containing the Same".
WPIL, Derwent Publications, Ltd., AN 91–202622, & JP-A-3118311, May 20, 1991, "Cosmetic—Material For Moisturising–Contg.–Siloxane—With Hydrogenated–Abietic–Ester Substits. and Poly:Ol Moisturising CPD.".
File Supplier PAJ/JP0 & JP-A-2229106, "Solid—Cosmetic—".
WPIL, Derwent Publications, Ltd., An 87–132507, & JP-A-62072607, Apr. 3, 1987, "Hair—Rinse Compsn. for Imparting Lustre to—Hair—Contains Quat. Ammonium—Cholesteryl—Ester".
WPIL, Derwent Publications, Ltd., An 86–315327, & JP-A-61 233 099, Oct. 17, 1986, "Cleaning Compsn. for Human—Skin—Etc. Requiring No Rinsing—Comprises Solid Wax,—Silicone—Oil, Nonionic and Anionic Surfactants, Water–Soluble Polymer and Water".

Primary Examiner—Peter F. Kulkosky
Attorney, Agent, or Firm—Oblon, Spivak, McClelland, Maier & Neustadt

[57] ABSTRACT

Silicone derivatives having polysiloxane units represented by the following general formulae (A), (B) and (C):

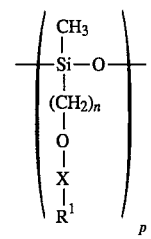

(A)

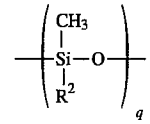

(B)

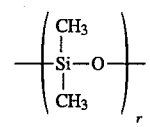

(C)

are useful as ingredients in cosmetic compositions.

6 Claims, No Drawings

CHOLESTERYL SILICONE DERIVATIVE AND COSMETIC COMPOSITION COMPRISING THE SAME

This application is a Continuation of application Ser. No. 07/913,719, filed on Jul. 16, 1992, now abandoned.

BACKGROUND OF THE INVENTION

1. Field of the Invention

The present invention relates to novel silicone derivatives and cosmetic compositions which comprise such a silicone derivative, and exhibit good compatibility with the skin and moreover afford an excellent moisturized feel upon use.

2. Description of the Background

Silicone oils have been widely used as oily substances for cosmetic compositions to date due to the fact that they are excellent in lubricating property, water repellency, gloss-imparting ability, stability and safety.

Among the silicone oils, high-molecular weight dimethylpolysiloxanes have been used most commonly as oily substances for cosmetic compositions. However, they involve drawbacks that they are poor in solubility in polar oily substances and water, and moreover difficult to emulsify in a system containing a hydrocarbon type oily substance. Furthermore, cosmetic compositions containing such a silicone oil have a squeaky feel peculiar to the silicone oil and are also poor in compatibility with the skin, and hence have been not wholly satisfactory from the viewpoint of feel such as a moisturized feel.

Accordingly, there has been a demand for development of a silicone derivative which does not suffer from the above-described drawbacks and affords an excellent feeling upon use, which is not found in the conventional silicone oils.

SUMMARY OF THE INVENTION

Accordingly, it is an object of the present invention to provide novel silicone derivatives which exhibit good compatibility with the skin.

It is another object of the present invention to provide novel silicone derivatives which provide good feeling to the skin when used as a cosmetic.

It is another object of the present invention to provide novel silicone derivatives which exhibit a reduced tendency to result in a squeaky feeling on-the skin.

It is another object of the present invention to provide novel silicone derivatives which are compatible with hydrocarbon type oily substances, polar oily substances, and water, and can stably maintain systems, such as emulsions, containing these substances.

It is another object of the present invention to provide novel cosmetic compositions which contain such silicone derivatives.

These and other objects, which will become apparent during the following detailed description, have been achieved by the inventors' discovery that a silicone derivative (1) having polysiloxane units represented by the general formulae (A), (B) and (C), which will be described subsequently, is good in compatibility with hydrocarbon type oily substances, polar oily substances, water and the like and can stably maintain systems containing them, and cosmetic compositions containing this silicone derivative are good in compatibility to the skin, do not have a squeaky feel peculiar to silicone oils and give an excellent moisturized feeling upon use.

In a first aspect of the present invention, there is thus provided a silicone derivative (1) having polysiloxane units represented by the following general formulae (A), (B) and (C):

$$\left( \begin{array}{c} CH_3 \\ | \\ -Si-O- \\ | \\ (CH_2)_n \\ | \\ O \\ | \\ X \\ | \\ R^1 \end{array} \right)_p \quad (A)$$

$$\left( \begin{array}{c} CH_3 \\ | \\ -Si-O- \\ | \\ R^2 \end{array} \right)_q \quad (B)$$

$$\left( \begin{array}{c} CH_3 \\ | \\ -Si-O- \\ | \\ CH_3 \end{array} \right)_r \quad (C)$$

wherein $R^1$ is a polycyclic hydrocarbon group having 7–30 carbon atoms, $R^2$ denotes a straight-chain, branched, alicyclic or aromatic hydrocarbon group having 2–30 carbon atoms, X is a single bond, —COO—, —CH$_2$CH$_2$—OCOO— or —CH$_2$COO—, n stands for an integer of 2–16, p is an integer of 1–100, and q and r are each independently an integer of 0–100.

In another aspect of the present invention, there is also provided a cosmetic composition comprising this silicone derivative (1).

The silicone derivative (1) according to the present invention is good in compatibility with hydrocarbon type oily substances, polar oily substances, water and the like and can stably maintain systems containing them and hence is useful as an oily substance for cosmetic compositions, which is widely applied. In addition, the silicone derivative (1) of the present invention is (1) liquid at room temperature, (2) low in viscosity and not sticky to the touch, (3) chemically stable, (4) extremely low in irritation to the skin, (5) good in compatibility with the skin owing to the similarity of its skeleton to the lipid between horny cells. Therefore, it is particularly useful as an oily substance for cosmetic compositions which are applied directly to the skin.

Besides, the cosmetic compositions containing the silicone derivative (1) according to this invention are good in conformability to the skin, greatly reduced in squeaky feel peculiar to silicone oils and give an excellent moisturized feel upon use.

DETAILED DESCRIPTION OF THE PREFERRED EMBODIMENTS

As illustrative examples of the polycyclic hydrocarbon group represented by $R^1$ and having 7–30 carbon atoms in the polysiloxane unit (A) of the silicone derivative (1) according to the present invention, may be mentioned a cholesteryl group, dihydrocholesteryl group, tetrahydroabiethyl group and the like. It is preferred that the polycyclic hydrocarbon of R' have 10–30 carbon atoms.

In the polysiloxane unit (B), the hydrocarbon group represented by $R^2$ is preferably a straight-chain or branched alkyl or alkenyl group having 2–30 carbon atoms, or an aromatic group such as a phenyl group, with a straight-chain or branched alkyl group having 2–30 carbon atoms being particularly preferred. As specific examples thereof, may be mentioned an ethyl group, propyl group, butyl group, hexyl group, heptyl group, octyl group, nonyl group, decyl group, tetradecyl group, hexadecyl group, octadecyl group, docosyl group and the like.

No particular limitation is imposed on the average molecular weight of the silicone derivative (1) of this invention. However, it is preferably 500–30,000 particularly 1,000–20,000. Besides, the molecular weight of the methylpolysiloxane moieties [the portions of —Si(CH$_3$)O—] in this silicone derivative (1) is preferably 10,000 or lower. Thus, the sum of p+q+r is typically an integer of 1 to 160, preferably 5 to 120.

No particular limitation is imposed on the combination of the siloxane unit of (A) with the other siloxane units (B) and (C) in the silicone derivative (1) of the present invention and on their combination form, so long as the siloxane unit (A) is contained therein. Namely, any one of the units (A) alone and the combinations of (A) with (B), of (A) with (C) and (A) with (B) and (C) may be chosen. Further, the units (A), (B) and (C) may be combined either at random or in the form of blocks. Thus, the present silicone derivatives include homopolymers of (A) and both random and block copolymers of (A) with (B) and/or (C). In all the cases, the units (A) and (B) may be selected independently from the permitted values even within a particular silicone derivative. Thus, the present derivatives include polymers in which two or more different (A) units and/or (B) units are present.

It is also to be understood that the extra valencies occurring on the terminal groups of the present .silicone derivatives are bonded to a suitable monovalent group, such as methyl group. It is further to be understood that when X is —CH$_2$CH$_2$—OCOO—, the bond from the methylene group is attached to the O bonded to X, and the bond from the carbonate moiety is attached to $R_1$. Similarly, when X is —CH$_2$COO—, the bond from the methylene group is attached to the O atom bonded to X, and the bond from the carboxylate moiety is attached to $R_1$.

The silicone derivative (1) according to the present invention can be prepared, for example, in accordance with any one of the following processes:

Process A:

A hydrogenpolysiloxane (2) having the polysiloxane units represented by the general formulae (B) and (C) and a polysiloxane unit represented by the following general formula (D):

$$\left[ \begin{array}{c} CH_3 \\ | \\ -Si-O- \\ | \\ H \end{array} \right]_p \quad (D)$$

wherein p has the same meaning as defined above is reacted with an olefin derivative (3) in the presence of a catalytic amount of H$_2$PtCl$_6$ catalyst (hydrogen hexachloroplatinate (IV)) under conditions of room temperature or heating in accordance with the following reaction formula, thereby obtaining the silicone derivative (1) of the present invention.

Hydrogenpolysiloxane +

(2)

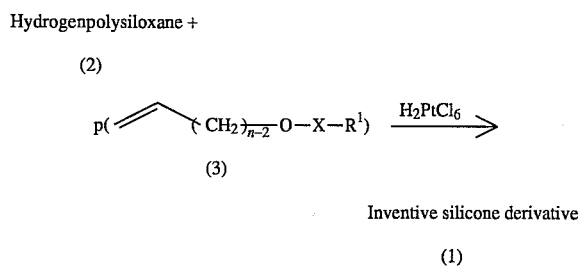

(3)

Inventive silicone derivative (1)

wherein $R^1$, X, n and p have the same meaning as defined above.

Among the hydrogenpolysiloxanes (2) used as a raw material in this process, those in which q is O may be commercially available for use from, for example, Toshiba Silicone Co., Ltd. On the other hand, those in which q is other than O may be obtained, for example, by reacting a hydrogenpolysiloxane (4) having the polysiloxane units represented by the general formulae (C) and (D) and a polysiloxane unit represented by the following general formula (E):

$$\left[ \begin{array}{c} CH_3 \\ | \\ -Si-O- \\ | \\ H \end{array} \right]_q \quad (E)$$

wherein q has the same meaning as defined above, with an olefin (5) in the presence of a catalytic amount of H$_2$PtCl$_6$ catalyst in accordance with the following reaction formula.

Hydrogenpolysiloxane + q × CH$_2$=CH—R$^3$ $\xrightarrow{H_2PtCl_6}$ (4) (5)

Hydrogenpolysiloxane (2)

wherein $R^3$ means a straight-chain, branched, alicyclic or aromatic hydrocarbon group having 1–28 carbon atoms, and q has the same meaning as defined above.

Further, the olefin derivative (3) used as a raw material in Process A may be obtained by reacting an alcohol (6) separately with an alkenyl chloride or bromide, an alkenyl chloroformate and an alkenyloxyacetyl chloride according to the kind of X, for example, in accordance with the following reaction formulae:

Ether:

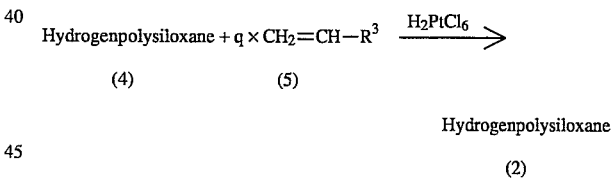

(6) (Br)

Alkenyloxycarbonic acid ester:

$$R^1OH + \diagup\!\!\!\diagup\!\!-(CH_2)_{\overline{n-2}}-OCOCl \longrightarrow$$
(6)

$$\diagup\!\!\!\diagup\!\!-(CH_2)_{\overline{n-2}}-OCOOR^1$$

Alpha-alkenyloxyacetic acid ester:

$$R^1OH + \diagup\!\!\!\diagup\!\!-(CH_2)_{\overline{n-2}}-OCH_2COCl \longrightarrow$$
(6)

$$\diagup\!\!\!\diagup\!\!-(CH_2)_{\overline{n-2}}-OCH_2COOR^1$$

Process B:

A chloroformate (8) is reacted with an alcohol-modified polysiloxane (7) having the polysiloxane units represented by the general formulae (B) and (C) and a polysiloxane unit represented by the following general formula (F):

$$\left[\begin{array}{c} CH_3 \\ | \\ -Si-O- \\ | \\ (CH_2)_n \\ | \\ O \\ | \\ (CH_2)_2 \\ | \\ OH \end{array}\right]_p \quad (F)$$

wherein n and p have the same meaning as defined above in accordance with the following reaction formula, thereby obtaining the silicone derivative (1) of the present invention, in which X is —CH$_2$CH$_2$—OCOO—.

$$\text{Alcohol-modified polysiloxane} + Cl-\overset{O}{\underset{\|}{C}}-OR^1 \times p \longrightarrow$$
(7)       (8)

Inventive silicone derivative
(1)

wherein R$^1$ and p have the same meaning as defined above.

The alcohol-modified polysiloxane (7) used as a raw material in this process can be synthesized by reacting the hydrogenpolysiloxane (2) with an alcohol (9) in accordance with the following reaction formula.

Hydrogenpolysiloxane +
(2)

$$\diagup\!\!\!\diagup\!\!-(CH_2)_{\overline{n-2}}-O(CH_2)_2OH \times p \longrightarrow$$
(9)

Alcohol-modified polysiloxane
(7)

wherein n and p have the same meaning as defined above.

The following compounds are typical silicone derivatives (1) obtained in the above-described manner.

$$\begin{array}{c} CH_3 \\ | \\ CH_3-Si-O \\ | \\ (CH_2)_3 \\ | \\ O \\ | \\ CH_2 \\ | \\ C=O \\ | \\ O \\ | \\ R^1 \end{array} \left[\begin{array}{c} CH_3 \\ | \\ -Si-O \\ | \\ CH_3 \end{array}\right]_{r1} \begin{array}{c} CH_3 \\ | \\ -Si-CH_3 \\ | \\ (CH_2)_3 \\ | \\ O \\ | \\ CH_2 \\ | \\ C=O \\ | \\ O \\ | \\ R^1 \end{array} \quad (1a)$$

$$\begin{array}{c} CH_3 \\ | \\ CH_3-Si-O \\ | \\ (CH_2)_3 \\ | \\ O \\ | \\ R^1 \end{array} \left[\begin{array}{c} CH_3 \\ | \\ -Si-O \\ | \\ CH_3 \end{array}\right]_{r2} \begin{array}{c} CH_3 \\ | \\ -Si-CH_3 \\ | \\ (CH_2)_3 \\ | \\ O \\ | \\ R^1 \end{array} \quad (1b)$$

$$\begin{array}{c} CH_3 \\ | \\ CH_3-Si-O \\ | \\ (CH_2)_3 \\ | \\ O \\ | \\ (CH_2)_2 \\ | \\ O \\ | \\ C=O \\ | \\ O \\ | \\ R^1 \end{array} \left[\begin{array}{c} CH_3 \\ | \\ -Si-O \\ | \\ CH_3 \end{array}\right]_{r3} \begin{array}{c} CH_3 \\ | \\ -Si-CH_3 \\ | \\ CH_3 \end{array} \quad (1c)$$

$$CH_3 \left[\begin{array}{c} CH_3 \\ | \\ -Si-O \\ | \\ CH_3 \end{array}\right]_{r4} \left[\begin{array}{c} CH_3 \\ | \\ -Si-O \\ | \\ (CH_2)_3 \\ | \\ O \\ | \\ C=O \\ | \\ O \\ | \\ R^1 \end{array}\right]_{p4} \begin{array}{c} CH_3 \\ | \\ -Si-CH_3 \\ | \\ CH_3 \end{array} \quad (1d)$$

$$\begin{array}{c} CH_3 \\ | \\ CH_3-Si-O \\ | \\ (CH_2)_3 \\ | \\ O \\ | \\ C=O \\ | \\ O \\ | \\ R^1 \end{array} \left[\begin{array}{c} CH_3 \\ | \\ -Si-O \\ | \\ CH_3 \end{array}\right]_{r5} \begin{array}{c} CH_3 \\ | \\ -Si-CH_3 \\ | \\ CH_3 \end{array} \quad (1e)$$

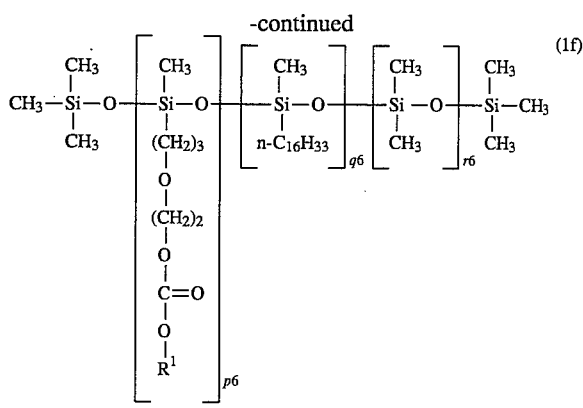

wherein $R^1$ has the same meaning as defined above, r1 and r2 denote independently a number of 0–160 on the average, r3 is a number of 0–160 on the average, r4 stands for a number of 0–160 on the average, p4 means a number of 1–80 on the average, r5 denotes a number of 0–160 on the average, p6 is a number of 1–80 on the average, q6 stands for a number of 1–80 on the average, and r6 means a number of 0–160 on the average.

Cosmetic compositions according to the present invention contain the above-described silicone derivative (1) as an oily substance for the cosmetic compositions. No particular limitation is imposed on the proportion thereof. In general, it is however incorporated in a proportion of 0.001–90 wt. % (hereinafter indicated merely by "%"), preferably 1–50%, based on the total weight of the composition.

In the cosmetic compositions according to the present invention, it is possible to use in combination in addition to the essential ingredient described above oily substances employed routinely in cosmetic compositions. As illustrative examples of such oily substances, may be mentioned cyclic silicones such as octamethylcyclotetrasiloxane, decamethylcyclopentasiloxane, dodecamethylcyclohexasiloxane; nonvolatile silicones such as methylpolysiloxane, dimethylpolysiloxane and methylphenylpolysiloxane; animal and vegetable oils and fats such as squalane and palm oil; and others including hydrocarbons, higher fatty acid esters, liquid paraffin and liquid isoparaffin.

Furthermore, in the cosmetic compositions of the present invention, ingredients, which are mixed routinely in cosmetic compositions, for example, solid and semisolid oils such as vaseline, lanolin, ceresin, microcrystalline wax, carnauba wax, candelilla wax, higher fatty acids and higher alcohols; water-soluble and oil-soluble polymers; coloring materials such as inorganic and organic pigments, silicon- or fluorine compound-treated inorganic and organic pigments, and organic dyes; surfactants such as anionic surfactants, cationic surfactants, nonionic surfactants, dimethyl-polysiloxane-polyoxyalkylene copolymers and polyether-modified silicones; and others including water, antiseptics, antioxidants, coloring matter, thickeners, pH regulators, perfume bases, ultraviolet absorbents, moisturizers, blood circulation-facilitating agents, cold sensation-imparting agents, antiperspirants, disinfectants and skin activators may be incorporated suitably as needed so far as they do not impede the effects of the inventive silicone derivative.

In the cosmetic compositions according to the present invention, no particular limitation is also imposed on their forms and kinds. They can be formulated in accordance with the methods known per se in the art and are applied to oily cosmetics, emulsified cosmetics, water-based cosmetics, lip sticks, cheek rouges, foundations, skin cleaners, hair shampoos, hair tonics, hair styling preparations, hair nourishing preparations, hair growth stimulants, etc.

Additional suitable ingredients and forms of the present cosmetic compositions, as well as a further discussion of methods of preparation, are given in Kirk-Othmer, *Encyclopedia of Chemical Technology*, 3rd ed. Wiley, volume 7, pp. 143–176, (1979), which is incorporated herein by reference.

Other features of the invention will become apparent in the course of the following descriptions of exemplary embodiments which are given for illustration of the invention and are not intended to be limiting thereof.

EXAMPLES

Example 1

Synthesis of Dihydrocholesterol-Modified Silicone (1A):

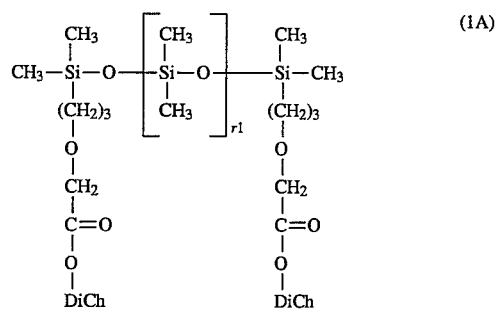

wherein r1 stands for a number of 18 on the average, and DiCh means dihydrocholesteryl group.

(a) Synthesis of dihydrocholesteryl allyloxyacetate (3a):

A 200-ml flask equipped with a dropping funnel and stirrer was charged with 28.1 g (72.3 mmols) of dihydrocholesterol, 11.4 g (145 mmols) of pyridine and 100 ml of dichloromethane. While stirring the contents at room temperature, 10.7 g (79.5 mmols) of allyloxyacetyl chloride was added to react them for 1 hour at room temperature. The reaction mixture was then washed with 3N hydrochloric acid, and the solvent was removed by distillation under reduced pressure. Thereafter, the residue was purified by chromatography on silica gel, thereby obtaining dihydrocholesteryl allyloxyacetate (3a) (35.1 g, yield: 99.7%).

(b) Synthesis of dihydrocholesterol-modified silicone (1A):

A 500-ml flask equipped with a condenser and stirrer was charged with 44.3 g (30 mmols) of a hydrogen-polysiloxane (product of Toshiba Silicone Co., Ltd.) represented by the following general formula (2a):

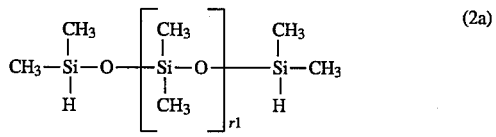

wherein r1 has the same meaning as defined above, 29.2 g (60 mmols) of dihydrocholesteryl allyloxyacetate (3a) obtained in the step (a), 0.03 g (0.3 mmol) of potassium acetate and 300 ml of isopropyl alcohol. The contents were added with 0.016 g (0.03 mmol) of $H_2PtCl_6 \cdot H_2O$ (hydrogen hexachloroplatinate. (IV) monohydrate), followed by agitation at 50° C. for 4 hours. After completion of the reaction, the solvent was removed by distillation under reduced pressure, and the residue was purified by chromatography on silica gel, thereby obtaining 55.5 g (yield: 75.5%) of the intended compound (1A) as a colorless oil. [Physical properties of dihydrocholesterol-modified silicone (1A)] $^1$H-NMR (CDCl$_3$, δ): −0.15–0.15(m, about 120H), 0.40–2.00(m,100H), 3.41(t,J=7.0 Hz,4H), 3.95(s,4H), 4.56–4.83(m,2H).

Example 2

Synthesis of Dihydrocholesterol-Modified Silicone (1B):

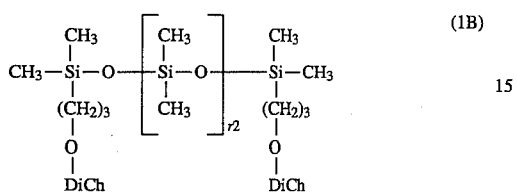

wherein r2 stands for a number of 9 on the average, and DiCh has the same meaning as defined above.

(a) Synthesis of allyl dihydrocholesteryl ether (2b):

A 500-ml flask equipped with a condenser and stirrer was charged with 4 g (100 mmols) of sodium hydride, 200 ml of tetrahydrofuran, 20 ml of dimethylformamide, 19.4 g (50 mmols) of dihydrocholesterol and 12.1 g (100 mmols) of allyl bromide. The contents were heated for 24 hours in a nitrogen stream to reflux them. The reaction mixture was then poured into water, and the resulting mixture was extracted with chloroform. The solvent was then removed by distillation under reduced pressure, and the residue was purified by chromatography on silica gel, thereby obtaining 21.1 g (yield: 98.4%) of allyl dihydrocholesteryl ether (2b).

(b) Synthesis of dihydrocholesterol-modified silicone (1B):

Following the same procedure as in Example 1(b) except that 22.1 g (15 mmols) of the hydrogenpolysiloxane (product of Toshiba Silicone Co., Ltd.) represented by the general formula (2a), 12.9 g (30 mmols) of allyl dihydrocholesteryl ether (2b) obtained in the step (a), 0.03 g (0.3 mmol) of potassium acetate, 0.016 g (0.03 mmol) of H$_2$PtCl$_6$·H$_2$O and 300 ml of isopropyl alcohol were used, the intended compound (1B) was obtained (yield: 62.9%). [Physical properties of dihydrocholesterol-modified silicone (1B)]$^1$H-NMR (CDCl$_3$, δ): −0.10–0.15(m, about 120H), 0.36–1.95(m, 100H), 3.01–3.25(m,2H), 3.33(t,J=7.2 Hz,4H).

Example 3

Synthesis of Cholesterol-Modified Silicone (1C):

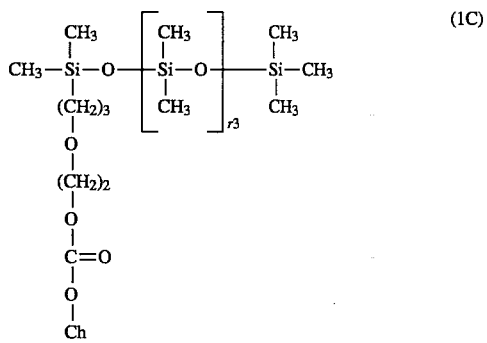

wherein r3 stands for a number of 23 on the average, and Ch denotes a cholesteryl group.

(a) Synthesis of allyl dihydrocholesteryl ether (2b):

A 200-ml flask equipped with a stirrer was charged with 24.7 g (11 mmols) of an alcohol-modified polysiloxane (product of Shin-Etsu Chemical Co., Ltd.) represented by the following general formula (7c):

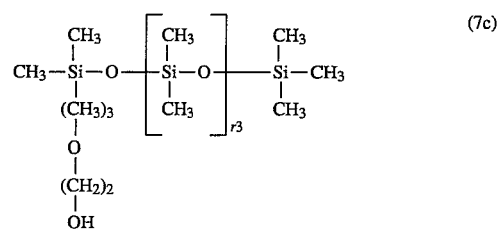

wherein r3 has the same meaning as defined above, 1.58 (20 mmols) of pyridine and 100 ml of dichloromethane. While stirring the contents at room temperature, 4.49 g (10 mmols) of cholesteryl chloroformate was added in several portions to react them for 15 hours at room temperature. The reaction mixture was then washed with water, and the solvent was removed by distillation under reduced pressure. Thereafter, the residue was purified by chromatography on silica gel, thereby obtaining 21.4 g (yield: 80.6%) of the intended compound (1C) as a colorless oil. [Physical properties of dihydrocholesterol-modified silicone (1C)] $^1$H-NMR (CDCl$_3$, δ): −0.11–0.19(m, about 180H), 0.37–0.55(m, 2), 0.60(s,3H), 0.72–2.02(m,36H), 2.25–2.42(m,4H), 3.35(t,J=7.0 Hz,2H), 3.51–3.64(m,2H), 4.02–4.34(m, 2H), 4.30–4.52(m,1H), 5.28–5.39 (m,1H).

Example 4

Synthesis of Tetrahydroabietyl Alcohol-Modified Silicone (1D):

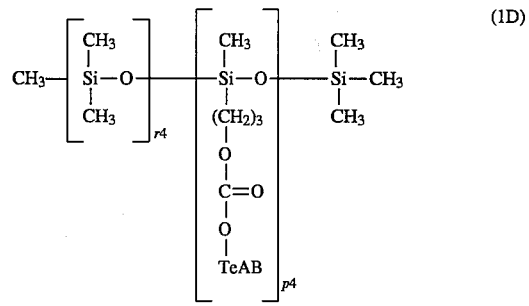

wherein TeAB means a tetrahydroabietyl group, r4 stands for a number of 81 on the average, and p4 denotes a number of 21 on the average.

(a) Synthesis of allyl tetrahydroabietyl carbonate (3d):

Following the same procedure as in Example 1(a) except that 29.2 g (100 mmols) of tetrahydroabietyl alcohol, 9.4 g (120 mmols) of pyridine, 13.2 g (110 mmols) of allyl chloroformate and 100 ml of dichloromethane were used, 32.4 g (yield: 85.8%) of allyl tetrahydroabietyl carbonate (3d) was obtained.

(b) Synthesis of tetrahydroabietyl alcohol-modified silicone (1D):

A 200-ml flask equipped with a condenser and stirrer was charged with 36.7 g (5 mmols) of a hydrogenpolysiloxane (product of Toshiba Silicone Co., Ltd.) represented by the following general formula (2d):

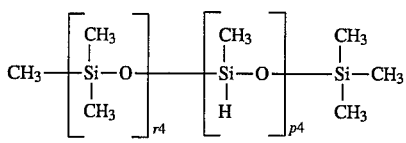

wherein r4 and p4 have the same meaning as defined above, 50 ml of isopropyl alcohol, 0.098 g (1 mmol) of potassium acetate, 0.052 g (0.1 mmol) of $H_2PtCl_6 \cdot H_2O$, 28.2 g (75 mmols) of the allyl tetrahydroabiethyl carbonate and 16.8 g (75 mmols) of 1-hexadecene. The contents were stirred for 3 hours at 50° C. The solvent and excess amounts of the raw material were then removed from the reaction mixture by distillation under reduced pressure (230° C./0.01 Torr), and the residue was decolored with activated carbon, thereby obtaining 46.4 g (yield: 70.3%) of the intended compound (1D) as a colorless oil. [Physical properties of tetrahydroabietyl alcohol-modified silicone (1D)] $^1$H-NMR (CDCl$_3$, δ): −0.10–0.16(bs, about 560H), 0.35–0.60(m, about 40H), 0.70–2.00(m, about 660H), 3.66–4.02(m, about 18H), 4.02–4.31(m, 18H).

Example 5

Moisturizing Cream

| <Composition> | (%) |
| --- | --- |
| 1) Compound (1A) | 10.0 |
| 2) Solid paraffin | 2.0 |
| 3) Cetyl 2-ethylhexanoate | 5.0 |
| 4) Lanolin | 5.0 |
| 5) Bees wax | 2.0 |
| 6) Stearyl alcohol | 4.0 |
| 7) Self-emulsifiable glycerol monostearate | 1.5 |
| 8) Polyoxyethylene sorbitan monooleate (20 E.O., E.O. = unit of ethylene oxide) | 1.0 |
| 9) Ethyl paraben | Suitable amount |
| 10) Methyl paraben | Suitable amount |
| 11) Perfume base | Suitable amount |
| 12) Purified water | Balance |
| Total | 100.0 |

<Formulation process>

The components 1) through 8) were maintained at 70° C. while melting them under heat. The components 9), 10) and 12) were also maintained at 70° C. while mixing them under heat and was added with the mixture of the components 1) through 8) to emulsify the resulting mixture in an emulsifier. The resulting emulsion was cooled to 40° C. while stirring it, to which the component 11) was added to intimately mix them. The resulting mixture was cooled down to 30° C. by a heat exchanger to formulate a moisturizing cream.

The moisturizing cream thus obtained gave users a moist feeling, was not very sticky to the touch and excellent in water-retaining ability and feeling upon use.

Example 6

Milky Lotion

A milky lotion having the following composition was formulated in a similar manner to Example 5.

| <Composition> | (%) |
| --- | --- |
| 1) Compound (1B) | 1.0 |
| 2) Cetanol | 0.5 |
| 3) Vaseline | 1.0 |
| 4) Squalane | 4.0 |
| 5) Liquid paraffin | 5.0 |
| 6) Stearic acid | 2.0 |
| 7) Polyoxyethylene oleyl ether (20 E.O.) | 2.0 |
| 8) Triethanolamine | 1.0 |
| 9) Ethyl paraben | Suitable amount |
| 10) Perfume base | Suitable amount |
| 11) Purified water | Balance |
| Total | 100.0 |

The milky lotion thus obtained gave users a moisturized feeling, was good in compatibility with the skin and excellent in feeling upon use.

Example 7

Lip Stick

A lip stick having the following composition was prepared in a similar manner to Example 5.

| <Composition> | (%) |
| --- | --- |
| 1) Compound (1C) | 30.0 |
| 2) Carnauba wax | 2.0 |
| 3) Ceresin | 4.0 |
| 4) Candelilla wax | 5.0 |
| 5) Microcrystalline wax | 2.0 |
| 6) Bees wax | 3.0 |
| 7) Lanolin | 3.0 |
| 8) Castor oil | 20.0 |
| 9) Hexadecyl alcohol | 20.0 |
| 10) Glycerol monostearate | 2.0 |
| 11) Titanium oxide | 2.0 |
| 12) Pigment (Red Color No. 202) | 2.0 |
| 13) Pigment (Red Color No. 204) | 1.0 |
| 14) Pigment (Yellow Color No. 4, Al rake) | 3.0 |
| 15) Antioxidant | Suitable amount |
| 16) Perfume base | Suitable amount |
| Total | 100.0 |

The lip stick thus obtained gave users a moisturized feeling, was not very sticky to the touch and excellent in feeling upon use.

Example 8

Creamy Foundation

A creamy foundation having the following composition was prepared in a similar manner to Example 5.

| <Composition> | (%) |
| --- | --- |
| 1) Compound (1D) | 10.0 |
| 2) Liquid paraffin | 8.0 |
| 3) Squalane | 8.0 |
| 4) Neopentyl glycol dioctanoate | 3.0 |
| 5) Sorbitan sesquiisostearate | 7.0 |
| 6) Aluminum distearate | 0.2 |
| 7) Magnesium sulfate | 0.7 |

-continued

| <Composition> | (%) |
|---|---|
| 8) Methyl paraben | 0.1 |
| 9) Titanium oxide | 8.0 |
| 10) Talc | 5.0 |
| 11) Sericite | 2.0 |
| 12) Iron oxide red | 0.4 |
| 13) Yellow iron oxide | 0.7 |
| 14) Black iron oxide | 0.1 |
| 15) Perfume base | Suitable amount |
| 16) Purified water | Balance |
| Total | 100.0 |

The creamy foundation thus obtained gave users a moisturized feeling, was not very sticky to the touch and excellent in water-retaining ability and feeling upon use.

Obviously, numerous modifications and variations of the present invention are possible in light of the above teachings. It is therefore to be understood that, within the scope of the appended claims, the invention may be practiced otherwise than as specifically described herein.

What is claimed is:

1. A silicone derivative (1) having polysiloxane units represented by the following general formula (1b):

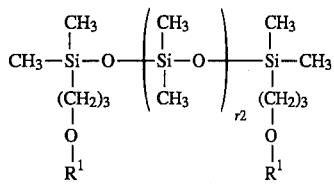
(1b)

wherein $R^1$ is a cholesteryl or dihydrocholesteryl group, and r2 is a number of 9–160 on the average, said silicone derivative having an average molecular weight of 1,000 to 20,000.

2. A cosmetic composition, comprising a silicone derivative having polysiloxane units represented by the following general formula (1b):

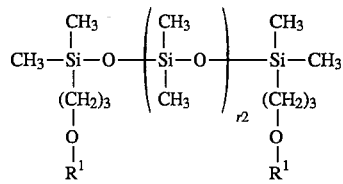
(1b)

wherein $R^1$ is a cholesteryl or dihydrocholesteryl group, and r2 is a number of 9–160 on the average, said silicone derivative having an average molecular weight of 1,000 to 20,000, and a cosmetically acceptable carrier or excipient.

3. The cosmetic composition of claim 2, wherein said silicone derivative is present in a proportion of 0.001 to 90 wt. % based on the total weight of the composition.

4. The cosmetic composition of claim 2, wherein said silicone derivative is present in a proportion of 1–50 wt. %, based on the total weight of the composition.

5. The cosmetic composition of claim 2, further comprising a compound selected from the group consisting of octamethylcyclotetrasiloxane, decamethylcyclopentasiloxane, dodecamethylcyclohexasiloxane, methylpolysiloxane, dimethylpolysiloxane, methylphenylpolysiloxane, squalane, palm oil, higher fatty acid esters, liquid paraffin, liquid isoparafin, vaseline, lanoline, ceresin, microcrystalline wax, carnauba wax, candelilla wax, higher fatty acids, higher alcohols, water-soluble and oil-soluble polymers, inorganic and organic pigments, silicon- of fluorine compound-treated inorganic and organic pigments, organic dyes, anionic surfactants, cationic surfactants, nonionic surfactants, dimethyl-polysiloxane-polyoxyalkylene copolymers, polyether-modified silicones, water, antiseptics, antioxidants, thickeners, pH regulators, perfume bases, ultraviolet absorbents, moisturizers, blood circulation-facilitating agents, cold sensation-imparting agents, antiperspirants, disinfectants, and skin activators.

6. The cosmetic composition of claim 2, which is a lip stick, cheek rouge, foundation, skin cleaner, hair shampoo, hair tonic, hair styling preparation, hair nourishing preparation, or hair growth stimulant.

* * * * *